(12) United States Patent
Kieval (10) Patent No.: US 8,214,050 B2
(45) Date of Patent: Jul. 3, 2012

(54) METHOD FOR MONITORING PHYSIOLOGICAL CYCLES OF A PATIENT TO OPTIMIZE PATIENT THERAPY

(75) Inventor: Robert S. Kieval, Medina, MN (US)

(73) Assignee: CVRx, Inc., Minneapolis, MN (US)

( * ) Notice: Subject to any disclaimer, the term of this patent is extended or adjusted under 35 U.S.C. 154(b) by 804 days.

(21) Appl. No.: 12/347,813

(22) Filed: Dec. 31, 2008

(65) Prior Publication Data

US 2009/0198303 A1 Aug. 6, 2009

Related U.S. Application Data

(60) Provisional application No. 61/018,195, filed on Dec. 31, 2007.

(51) Int. Cl.
*A61B 5/04* (2006.01)
(52) U.S. Cl. ......................................................... 607/44
(58) Field of Classification Search .................. 607/42, 607/44; 600/529, 533
See application file for complete search history.

(56) References Cited

U.S. PATENT DOCUMENTS

| | | | |
|---|---|---|---|
| 5,313,953 A | 5/1994 | Yomtov et al. | |
| 6,522,926 B1 | 2/2003 | Kieval et al. | |
| 6,985,774 B2 | 1/2006 | Kieval et al. | |
| 7,139,610 B2 * | 11/2006 | Ferek-Petric | 607/27 |
| 7,158,832 B2 | 1/2007 | Kieval et al. | |
| 7,480,532 B2 | 1/2009 | Kieval et al. | |
| 7,499,747 B2 | 3/2009 | Kieval et al. | |
| 7,623,926 B2 | 11/2009 | Rossing et al. | |
| 7,840,271 B2 | 11/2010 | Kieval et al. | |
| 7,907,998 B2 * | 3/2011 | Arad (Abboud) | 600/547 |
| 2005/0154418 A1 | 7/2005 | Kieval et al. | |
| 2005/0251212 A1 | 11/2005 | Kieval et al. | |
| 2006/0004417 A1 | 1/2006 | Rossing et al. | |
| 2006/0074453 A1 | 4/2006 | Kieval et al. | |
| 2006/0293712 A1 | 12/2006 | Kieval et al. | |

OTHER PUBLICATIONS

Warzel et al., The Effect of Time of Electrical Stimulation of the Carotid Sinus on the Amount of Reduction in Arterial Pressure, Pflugers Arch., 33:39-44, 1972.
Webster, J.G., Design of Cardiac Pacemakers, pp. 171-172, IEEE Press, 1995.

* cited by examiner

*Primary Examiner* — Eric D. Bertram
(74) *Attorney, Agent, or Firm* — Patterson Thuente Christensen Pedersen, P.A.

(57) ABSTRACT

Improved methods for obtaining physiological parameters of a patient in accordance with various embodiments of the present invention can be used to monitor patient status and/or in conjunction with patient therapy. Physiological parameters can be monitored with an implantable device including a first lead and a second lead. Physiological parameters can be measured along at least three distinct vectors defined by the first lead and second lead, the first lead and an electrode located on the device body, and the second lead an the electrode. An output indicative of the physiological parameter can then be provided. Therapy, such as baroreflex therapy, can optionally be optimized based on the physiological measurements.

10 Claims, 11 Drawing Sheets

METHOD FOR MONITORING PHYSIOLOGICAL CYCLES OF A PATIENT TO OPTIMIZE PATIENT THERAPY

RELATED APPLICATIONS

This application claims the benefit of U.S. Provisional Patent Application No. 61/018,195, filed Dec. 31, 2007.

FIELD OF THE INVENTION

The present invention relates generally to methods for monitoring physiological activity of a patient with an implantable device. More particularly, the present invention relates to detection of physiological parameters of a patient along at least three vectors, which can then be used to optimize patient therapy.

BACKGROUND OF THE INVENTION

Electrocardiograms (ECG or EKG) are commonly used to monitor and diagnose heart conditions. An ECG is a recording made by an electrocardiograph of electric waves generated during activity in the heart. To measure an ECG, electrodes, or electrical contacts, are placed on the skin. With each heart beat, an electrical impulse or wave travels through the heart, which, in turn, causes the heart muscles to pump blood from the heart to the rest of the body. The ECG records the voltage difference between pairs of electrodes and displays the rhythm of the heart and weaknesses that may be present in different parts of the heart.

In electrocardiography, a "lead" refers to a pair of electrodes that form an imaginary line in a patient along which electrical signals are measured. Three external leads, known as limb leads, form the three legs of what is known in the art as Einthoven's triangle. Einthoven's triangle defines an imaginary equilateral triangle having the heart at its center. Lead I is defined by a vector extending from a negative electrode on the right arm to a positive electrode on the left arm. Lead II is defined by a vector extending from the negative electrode on the right arm to a positive electrode on the left leg. Lead III is defined by a vector extending from a negative electrode on the left arm to the positive electrode on the left leg.

Current implantable cardiac rhythm management devices typically detect cardiac electrical activity between electrodes in or around the heart and the pulse generator, or between two electrodes on the pulse generator. The Reveal® Plus by Medtronic is a subcutaneously implantable loop recorder that can measure and record ECG data. U.S. Pat. No. 5,313,953 by Yomtov et al. discloses an implantable cardiac monitor with a subcutaneous lead proximate the heart, which is designed to process ECG signals. Additionally, prior art pacemaker and defibrillator manufacturers use associated cardiac leads connected to a sense amplifier in implantable pulse generators to facilitate ECG inputs.

Prior art implantable therapy devices such as pacemakers, defibrillators, and other devices have also been used to monitor thoracic impedance to detect respiration-related conditions, such as "lung water" and minute ventilation. This has been accomplished with the use of typically a single electrode implanted within the thoracic cavity, and an implantable pulse generator. While these implantable transthoracic methods of monitoring respiration were sometimes sufficient for diagnostic purposes, their single vector measurement approach leaves room for improvement for monitoring respiration for the purpose of timing the delivery of a therapy.

Significantly, however, cardiac electrical activity occurs over multiple electrical planes and vectors. Typically, approaches used by the prior art to monitor cardiac electrical activity lack complete information because they only detect electrical activity along one vector, such as between an electrode on a cardiac lead and the pulse generator. Furthermore, the prior art does not permit monitoring multiple ECG leads with an implantable medical device and integrating multiple-lead ECG information by an implantable medical device.

Thus, there remains a need in the art to be able to monitor cardiac electrical activity with an implantable medical device that can detect the ECG along at least three vectors, providing more complete information about heart function than existing devices and permitting discrimination of pathological events that cannot be detected with single-vector devices. Additionally, there exists a need in the art for a method for measuring ECGs and analyzing cardiac output that is also capable of detecting a patient's rate of respiration.

SUMMARY OF THE INVENTION

Improved methods for obtaining physiological parameters of a patient in accordance with various embodiments of the present invention can be used to monitor patient status and/or in conjunction with patient therapy. Physiological parameters can be monitored with an implantable device including a first lead and a second lead. In one embodiment, the first lead is implanted on the left carotid sinus and the second lead is implanted on the right carotid sinus. Physiological parameters can be measured along at least three distinct vectors defined by a first lead electrode and a second lead electrode, the first lead electrode and an electrode located on the device body, and the second lead an the electrode. Measurement across at least three vectors provides a more complete and accurate reading of patient physiological parameters than measurement across a single vector. An output indicative of the physiological parameter can then be provided. Therapy, such as baroreflex therapy, can optionally be optimized based on the physiological measurements.

In one embodiment, physiological parameters of a patient are monitored with an implantable monitoring system. Monitoring system can include a monitoring device operably connected to a first lead and a second lead. At least one physiological parameter of the patient can be measured by system along at least three distinct vectors. The first vector can be defined by an electrode on the first lead and an electrode on the second lead, the second vector by the electrode on the first lead and an electrode integrated into the monitoring device and the third vector by the electrode on the second lead and the electrode of the monitoring device. An output indicative of the physiological parameter can be provided to the care giver. In one embodiment, the measured parameter is voltage and the output is an ECG of the voltage. In another embodiment, the parameter is impedance and the output represents the patient's respiration. In a further embodiment, an output of the patient's respiration can be provided based on voltage measurements.

In another embodiment, baroreflex therapy can be optimized based on measurements of physiological parameters of a patient. A baroreflex device having an implantable pulse generator operably coupled to a first lead and a second lead can be implanted into the patient. The device can be used to measure at least one physiological parameter of the patient across at least three distinct vectors. The first vector can be defined by the first lead and the second lead, the second vector by the first lead and an electrode integrated into the monitoring device and the third vector by the second lead and the monitoring device. One or more baroreflex therapy pulses can be delivered through the first lead and second lead based on timing determined from the physiological parameter. In one embodiment, the physiological parameter is a voltage reported as an ECG reading, and the therapy pulses are configured to be delivered after a predetermined delay following an R-wave in the ECG. In another embodiment, the physiological parameter is impedance, which is used to determine the patient's respiration cycle, and therapy pulses are delivered during an expiration phase of the patient's respiration. In a further embodiment, both the patient's ECG and respiration are determined and therapy pulses are delivered after a predetermined delay following an R-wave that occurs during an expiration phase of the patient's respiration.

It should be understood that the intention is not to limit the present invention to any particular embodiments described. On the contrary, the intention is to cover all modifications, equivalents, and alternatives falling within the spirit and scope of the present invention as defined by the appended claims.

BRIEF DESCRIPTION OF THE DRAWINGS

This invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
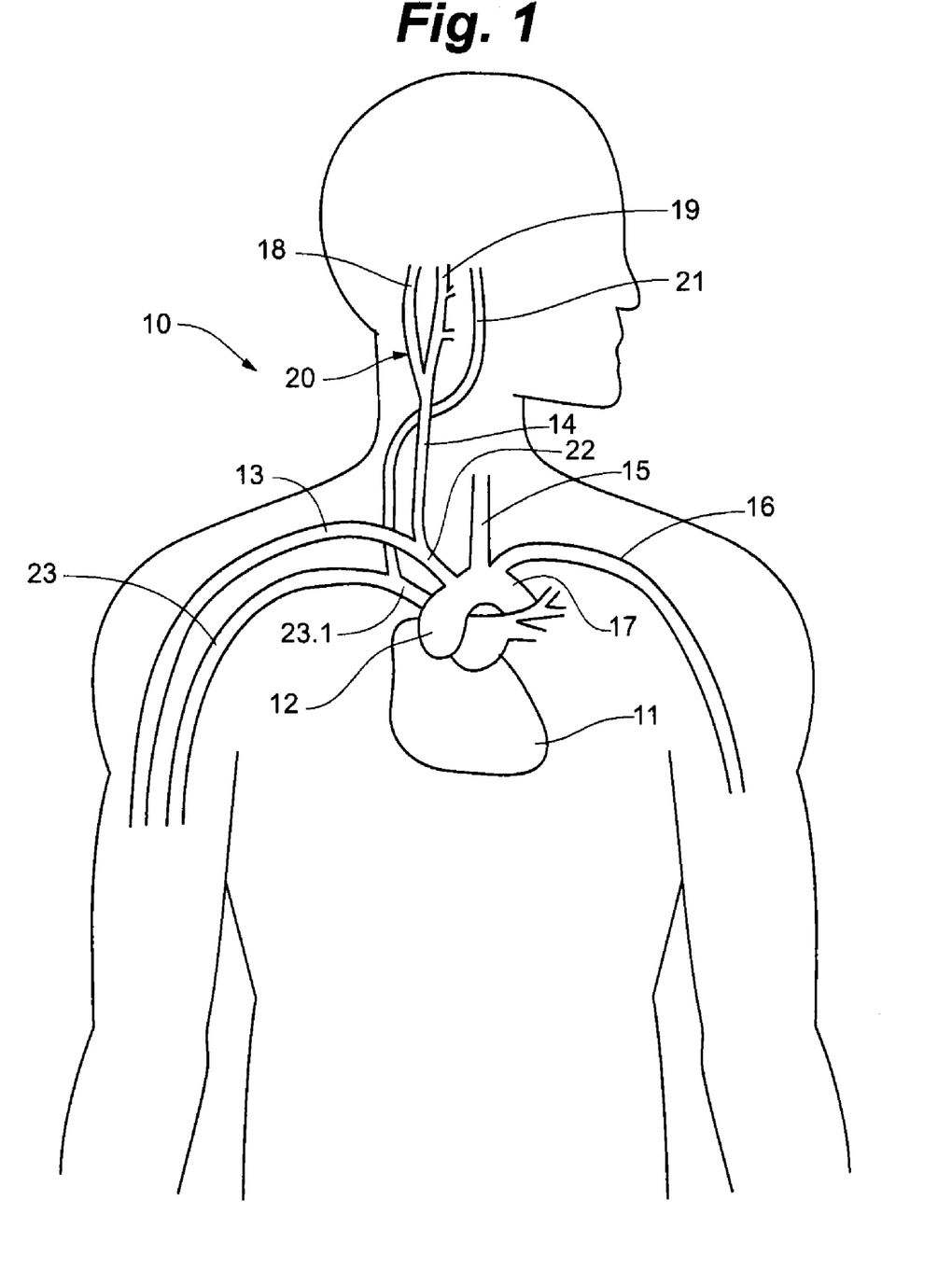
FIG. 1 is a schematic illustration of the upper torso of a human body showing the major arteries and veins and associated anatomy.

To better understand the present invention, it may be useful to explain some of the basic vascular anatomy associated with the cardiovascular system. Refer to FIG. 1 which is a schematic illustration of the upper torso of a human body 10 showing some of the major arteries and veins of the cardiovascular system. The left ventricle of the heart 11 pumps oxygenated blood up into the aortic arch 12. The right subclavian artery 13, the right common carotid artery 14, the left common carotid artery 15, and the left subclavian artery 15 branch off the aortic arch 12 proximal of the descending thoracic aorta 17. Although relatively short, a distinct vascular segment referred to as the brachiocephalic artery 22 connects the right subclavian artery 13 and the right common carotid artery 14 to the aortic arch 12. The right carotid artery 14 bifurcates into the right external carotid artery 18 and the right internal carotid artery 19 at the right carotid sinus 20. Although not shown for purposes of clarity only, the left carotid artery 15 similarly bifurcates into the left external carotid artery and the left internal carotid artery at the left carotid sinus.

From the aortic arch 12, oxygenated blood flows into the carotid arteries 18/19 and the subclavian arteries 13/16. From the carotid arteries 18/19, oxygenated blood circulates through the head and cerebral vasculature and oxygen depleted blood returns to the heart 11 by way of the jugular veins, of which only the right internal jugular vein 21 is shown for sake of clarity. From the subclavian arteries 13/16, oxygenated blood circulates through the upper peripheral vasculature and oxygen depleted blood returns to the heart by way of the subclavian veins, of which only the right subclavian vein 23 is shown, also for sake of clarity. Deoxygenated blood from the upper torso and head eventually return to the heart 11 through the superior vena cava 23.1, shown diagrammatically only. The heart 11 pumps the oxygen-depleted blood through the pulmonary system where it is re-oxygenated. The re-oxygenated blood returns to the heart 11 which pumps the re-oxygenated blood into the aortic arch as described above, and the cycle repeats.

Within the walls of many veins, the pulmonary vasculature and the chambers of the heart, as in the walls of the carotid sinus, aorta and other arterial structures, there are baroreceptors. Baroreceptors are a type of stretch receptor used by the body to sense blood pressure and blood volume. An increase in blood pressure or volume causes the vascular wall to stretch, and a decrease in blood pressure or volume causes the vascular wall to return to its original size. In many vessels, such a cycle is repeated with each beat of the heart. In others, in particular some of the body's veins, the pressure and volume change more slowly. Because baroreceptors are located within the vascular wall, they are able to sense deformation of the adjacent tissue, which is indicative of a change in blood pressure or volume.

Figure 2:
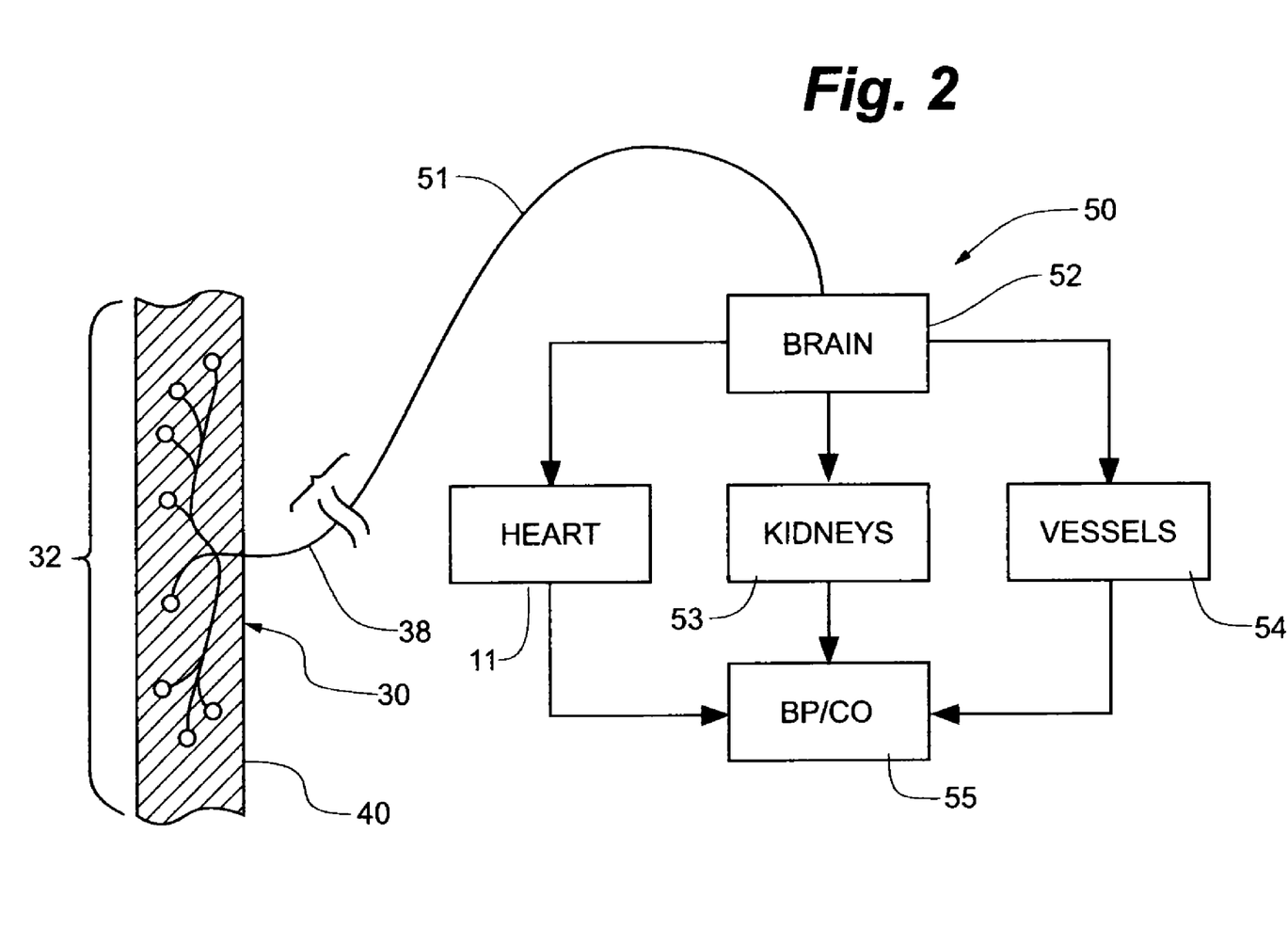
FIG. 2 is a cross-sectional schematic illustration of the autonomic nervous system.

Refer now to FIG. 2, which shows a schematic illustration of the autonomic nervous system of a patient, including baroreceptors 30 disposed in a generic vascular wall 40 and a schematic flow chart of the baroreflex system 50. Baroreceptors 30 are profusely distributed within the arterial walls 40 of the blood vessels and major arteries discussed previously, and are presently believed by the inventors to form an arbor 32 as is characteristic of the analogous receptors in the arterial system as described in commonly owned U.S. Pat. No. 6,522, 926 to Kieval et al, which is incorporated herein by reference. A baroreceptor arbor 32 would comprise a plurality of baroreceptors 30, each of which transmits baroreceptor signals to the brain 52 via nerve 38. The baroreceptors 30 may be so profusely distributed and arborized within the vascular wall 40 that discrete baroreceptor arbors 32 are not readily discernable. To this end, those skilled in the art will appreciate that the baroreceptors 30 shown in FIG. 2 are primarily schematic for purposes of illustration and discussion. In other regions, the baroreceptors may be so sparsely distributed that activation over a relatively greater length of the vein would be required than would be with an artery where the receptors might be more concentrated.

Baroreceptor signals in the arterial vasculature are used to activate a number of body systems which collectively may be referred to as the baroreflex system 50. For the purposes of the present invention, it will be assumed that the "receptors" in the venous and cardiopulmonary vasculature and heart chambers function analogously to the baroreceptors in the arterial vasculature, but such assumption is not intended to limit the present invention in any way. In particular, the methods described herein will function and achieve at least some of the stated therapeutic objectives regardless of the precise and actual mechanism responsible for the result. Moreover, the present invention may activate baroreceptors, mechanoreceptors, pressoreceptors, or any other venous heart, or cardiopulmonary receptors which affect the blood pressure, nervous system activity, and neurohormonal activity in a manner analogous to baroreceptors in the arterial vasculature. For convenience, all such venous receptors will be referred to collectively herein as "baroreceptors." Thus for discussion purposes, it will be assumed that baroreceptors 30 are connected to the brain 52 via the nervous system 51. Thus, the brain 52 is able to detect changes in blood pressure which are indicative of cardiac output and/or blood volume. If cardiac output and/or blood volume are insufficient to meet demand (i.e., the heart 11 is unable to pump sufficient blood), the baroreflex system 50 activates a number of body systems, including the heart 11, kidneys 53, vessels 54, and other organs/tissues. Such activation of the baroreflex system 50 generally corresponds to an increase in neurohormonal activity. Specifically, the baroreflex system 50 initiates a neurohormonal sequence that signals the heart 11 to increase heart rate and increase contraction force in order to increase cardiac output, signals the kidneys 53 to increase blood volume by retaining sodium and water, and signals the vessels 54 to constrict to elevate blood pressure. The cardiac, renal and vascular responses increase blood pressure and cardiac output 55, and thus increase the workload of the heart 11. In a patient with heart failure, this further accelerates myocardial damage and exacerbates the heart failure state.

The autonomic nervous system includes a sympathetic component and a parasympathetic component. The body uses these two systems to regulate blood pressure. The parasympathetic nervous system has a complementary relationship with the sympathetic nervous system. Stimulation of the parasympathetic nervous system generally causes a decrease in blood pressure, whereas stimulation of the sympathetic nervous system generally causes blood pressure to increase.

Baroreflex modulation therapy systems are used to treat patients with resistant hypertension by activating or modulating baroreceptors or other tissues capable of creating a change in the baroreflex system. Examples of such systems include The RHEOS System by CVRx, and the devices, systems, and methods described in U.S. Pat. Nos. 6,522,926, 6,985,774, 7,158,832, 7,480,532, 7,499,747, and 7,840,271, and Published U.S. patent application Ser. Nos. 2006/0004417 and 2006/0074453, all of which are hereby incorporated by reference and are commonly assigned to the assignee of the present application.

Figure 3:
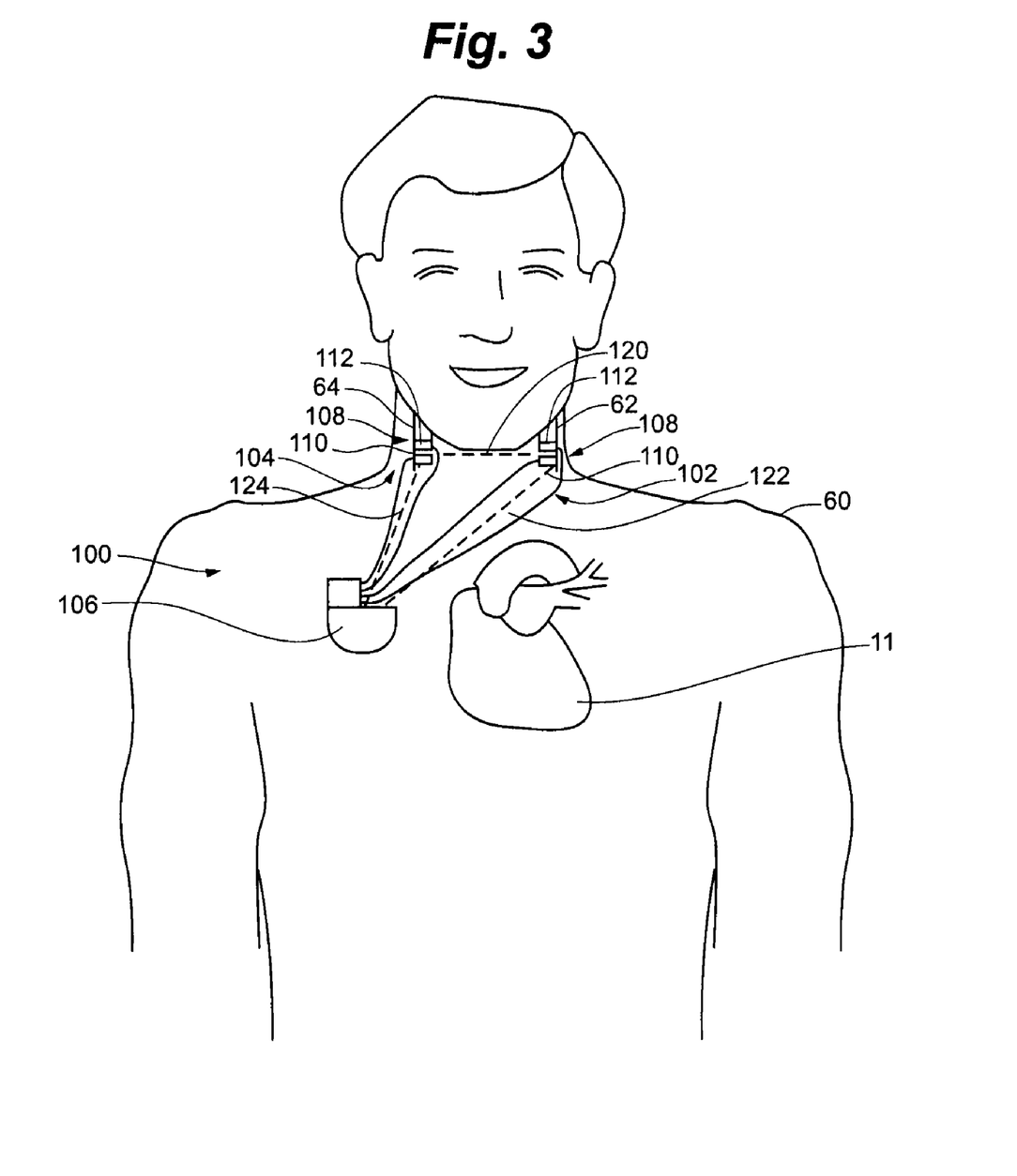
FIG. 3 is a simplified schematic view of a baroreflex therapy device according to an embodiment of the present invention implanted in a patient.

In one embodiment of the present invention depicted in FIG. 3, a baroreflex modulation therapy system 100 comprises two leads 102, 104, each including an electrode assembly 108, and an implantable pulse generator (IPG) 106. Rather than being located within the thoracic cavity of a patient 60, the leads 102, 104 are implanted outside the chest cavity, such as on or near the carotid sinus. IPG can be implanted on either side of the patient's chest. Each electrode assembly 108 can include an anode 110 and a cathode 112. In one embodiment, one lead 102 is located on the left carotid sinus 62 or left carotid artery and the other lead 104 is located on the right carotid sinus 64 or right carotid artery. In other embodiments, leads 102, 104, can be implanted in other areas of the body, such as, for example, the pulmonary artery.

Baroreflex modulation therapy system 100 is capable of collecting ECG information from the patient by measuring electrical potential or voltage differences between the various elements of the system 100. The system can monitor electrical signals and measure potential differences sensed between the two leads 102, 104 as well as between either of the leads 102, 104 and an electrode integrated with the IPG 106, such as on the housing or header portion of IPG 106. For each lead 102, 104, either the anode 110 or cathode wire 112 can be used. The lead 102—lead 104 vector 120 replicates Lead I of Einthoven's Triangle. The right lead 104—IPG 106 vector 122 replicates Lead II, and the left lead 102—IPG 106 replicates Lead III. With this arrangement, system can detect ECG information along at least three vectors. Because a single vector is not likely to provide a complete picture of the electrical activity in the heart, measuring across multiple vectors, by measuring potential differences between various elements, is advantageous.

Figure 4:
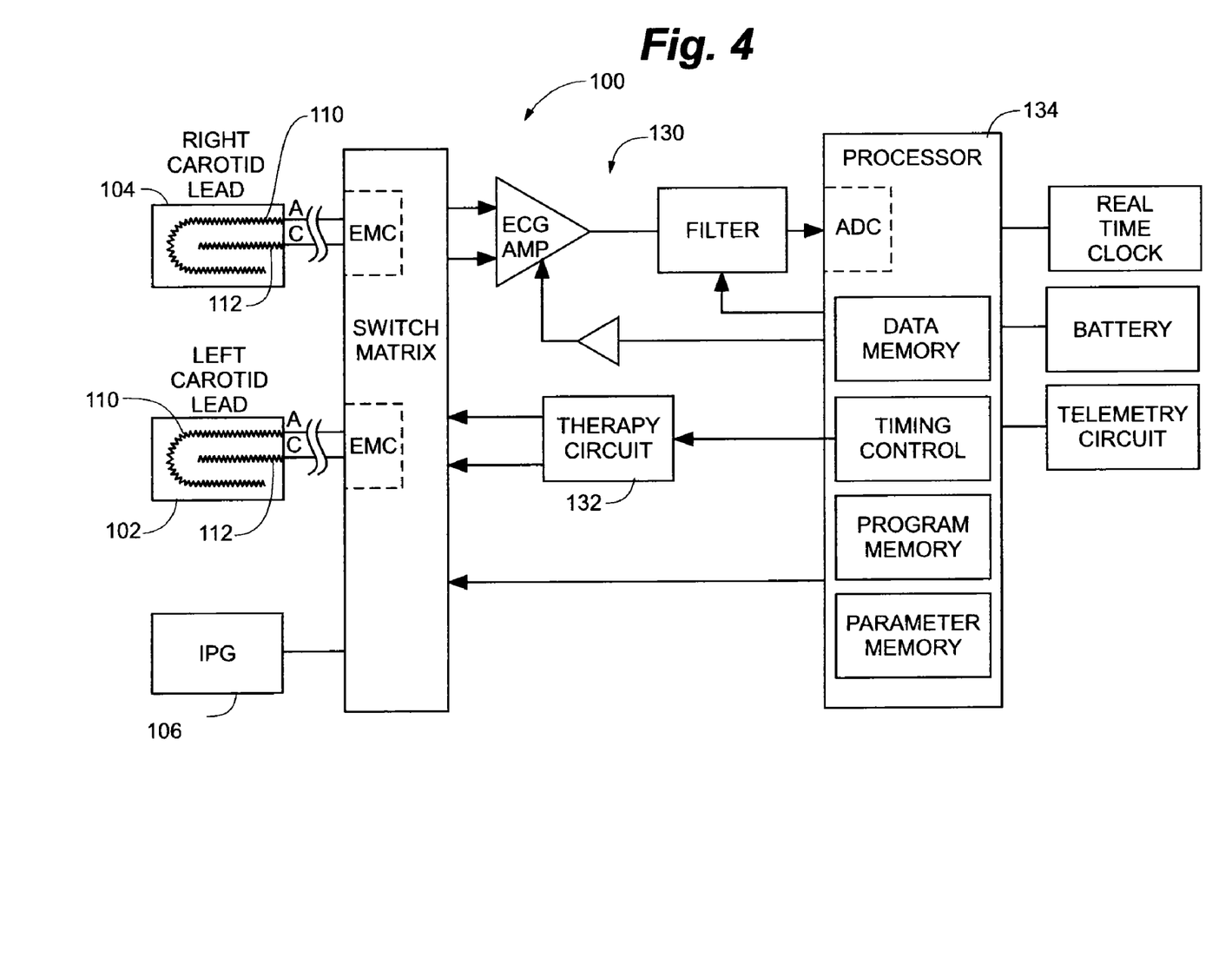
FIG. 4 is a schematic diagram of a baroreflex modulation therapy system according to an embodiment of the present invention.

FIG. 4 depicts a block diagram further illustrating baroreflex modulation therapy system 100. System 100 can include ECG measuring circuitry 130 configured to obtain ECG measurements through a combination of leads 102, 104 and IPG 106. System 100 can also include a therapy circuit 132 for delivering therapeutic pulses through leads 102, 104. A processor 134 can control the application of ECG measuring circuitry 130 and therapy circuit 134. The configuration of anode 110 and cathode 112 are for illustrative purposes and should not be considered limiting.

ECG information obtained by baroreflex therapy system 100 can be used to provide diagnostic information to the physician regarding the cardiac rhythm status and/or to guide the timing and delivery of therapy by system 100. In one embodiment, the baroreflex modulation therapy system is capable of recording, storing, and/or transmitting cardiac ECG information for future access by caregivers or the patient. As described herein, delivery of therapy pulses by baroreflex modulation therapy system can be more effective and use less energy if delivered at times when the body is experiencing increased baroreflex signaling. These times of increased baroreflex modulation can be determined from the ECG information. In other embodiments, other implantable devices, such as, for example, pacemakers and implantable defibrillators, can be configured as described above to obtain patient physiological parameters along at least three vectors. Such information can then be used diagnostically and/or to optimize therapy provided by the devices.

Figure 5:
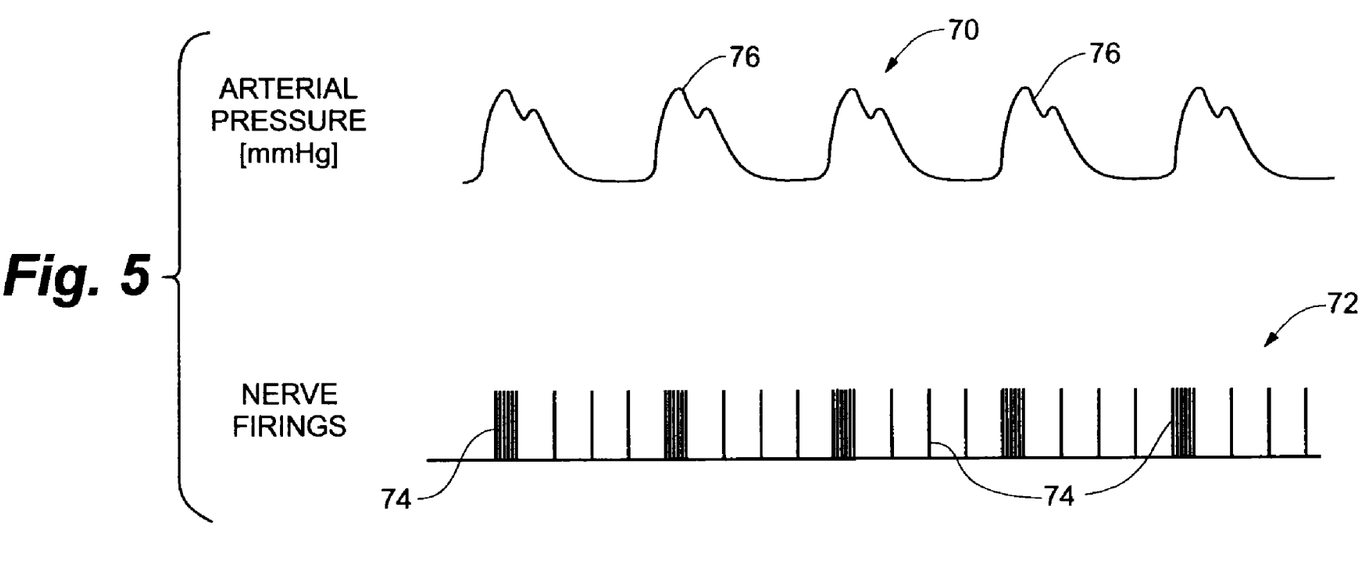
FIG. 5 is a graph illustrating a relationship between arterial blood pressure and autonomic nervous system activity.

Referring to FIG. 5, an arterial blood pressure waveform 70 and a symbolic plot of autonomic nervous system activity 72 illustrate the relationship between arterial blood pressure and autonomic nervous system activity. The vertical lines 74 in the plot of autonomic nervous system activity represent the firing of baroreceptors that affect the parasympathetic and sympathetic components of the autonomic nervous system. As can be seen in the Figure, the firing of baroreceptors increases when a wave of increasing arterial pressure passes. Each pulse of increased pressure 76 in FIG. 5 generally follows a corresponding contraction of the heart.

Figure 6:
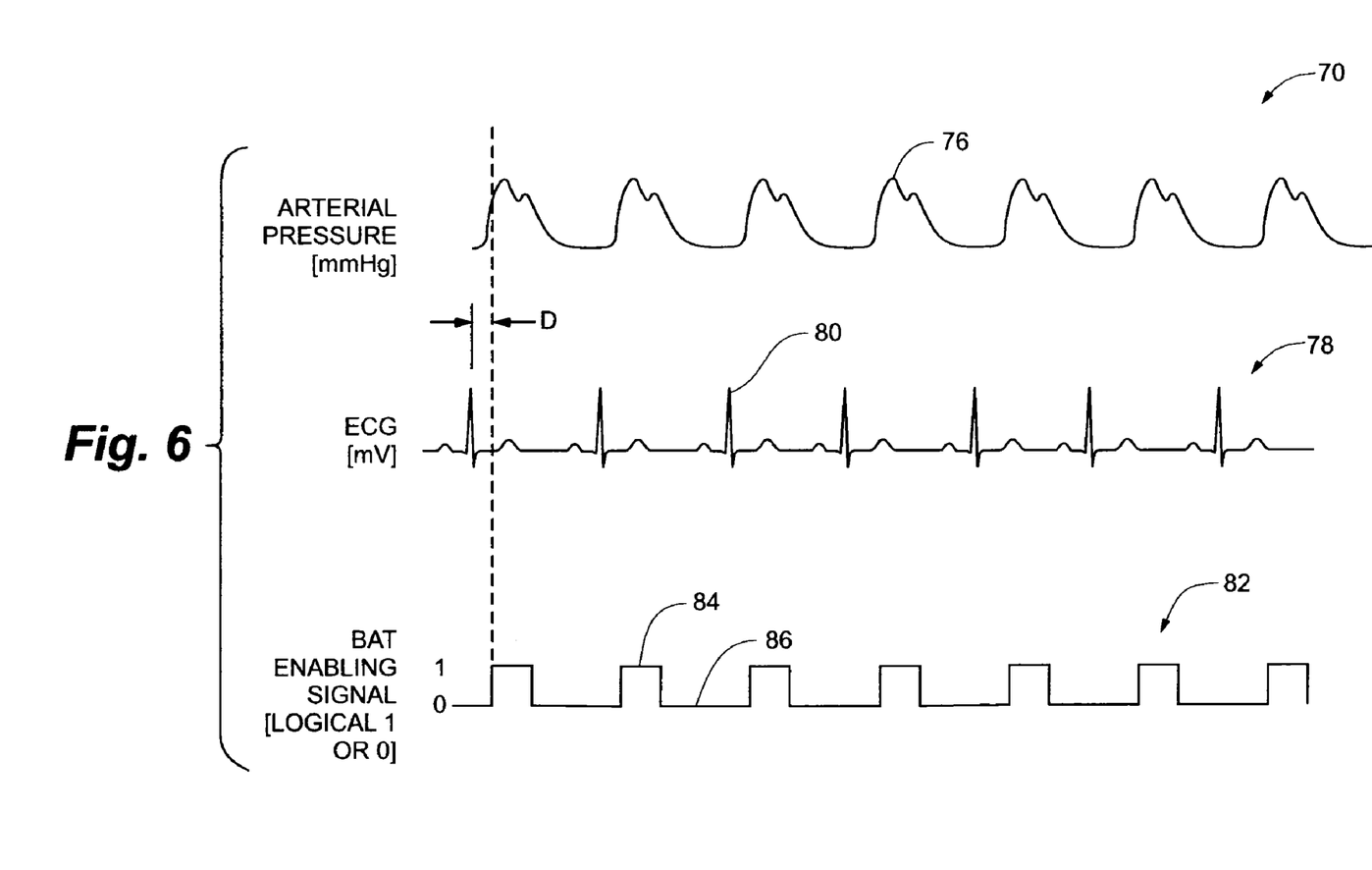
FIG. 6 is a graph illustrating a method of baroreflex modulation therapy according to an embodiment of the present invention.

FIG. 6 depicts a diagram illustrating the operation of a baroreflex modulation therapy system according to one embodiment of the present invention. The diagram depicts a waveform 70 of a patient's arterial blood pressure and a waveform 78 of an ECG reading from the patient. ECG reading can be obtained by measuring across at least three vectors utilizing a pair of leads and an IPG as described above. ECG waveform 78 includes a series of generally triangular-shaped R-waves 80. Each R-wave 80 is associated with the electrical activation of the ventricles associated with a single heart beat. By comparing the arterial pressure waveform 70 and the ECG waveform 78, it can be seen that each pulse of increased blood pressure 76 follows a corresponding contraction of the patient's heart, after a short delay. Each pulse of increased blood pressure 76 is expected to cause increased baroreflex activation in the patient. The diagram also depicts a baroreflex modulation therapy system control signal 82. The control signal 82 indicates when baroreflex modulation therapy is enabled 84 and where it is disabled 86.

In one embodiment, as shown in FIG. 6, there can be a time delay between the peak of each R-wave 80 and the delivery of a baroreflex therapy pulse 84. The magnitude of the time delay may be pre-selected to correspond with a selected phase of the cardiac cycle. Delivering the therapy pulses slightly after the detection of an R-wave during the systolic phase of the cardiac cycle causes the therapy to be delivered as a relatively high level of pressure passes through the patient's arterial system, and, accordingly, as the body is experiencing increased baroreflex modulation. Delivery of therapy pulses during this time therefore complements the natural autonomic nervous activity of the body. Timing delivery of therapy in this manner can allow baroreflex modulation therapy to achieve the same level of therapeutic effect with less energy. This can extend the battery life and may enable the use of smaller baroreflex modulation therapy devices than would otherwise be necessary. In one embodiment, baroreflex modulation therapy device can auto-adjust therapy in response to the sensed physiological information.

Baroreflex modulation therapy can also take advantage of a relationship between respiration and autonomic nervous system activity. The efficacy of baroreflex modulation therapy may be influenced by when therapy is delivered relative to the respiratory cycle. Changes in respiration during and resulting from baroreflex modulation therapy may also provide important clinical information, including the rate of respiration, the depth of respiration, and the phases of respiration (inspiration versus expiration) using a combination of extra-thoracic electrodes and the implantable pulse generator.

Figure 7:
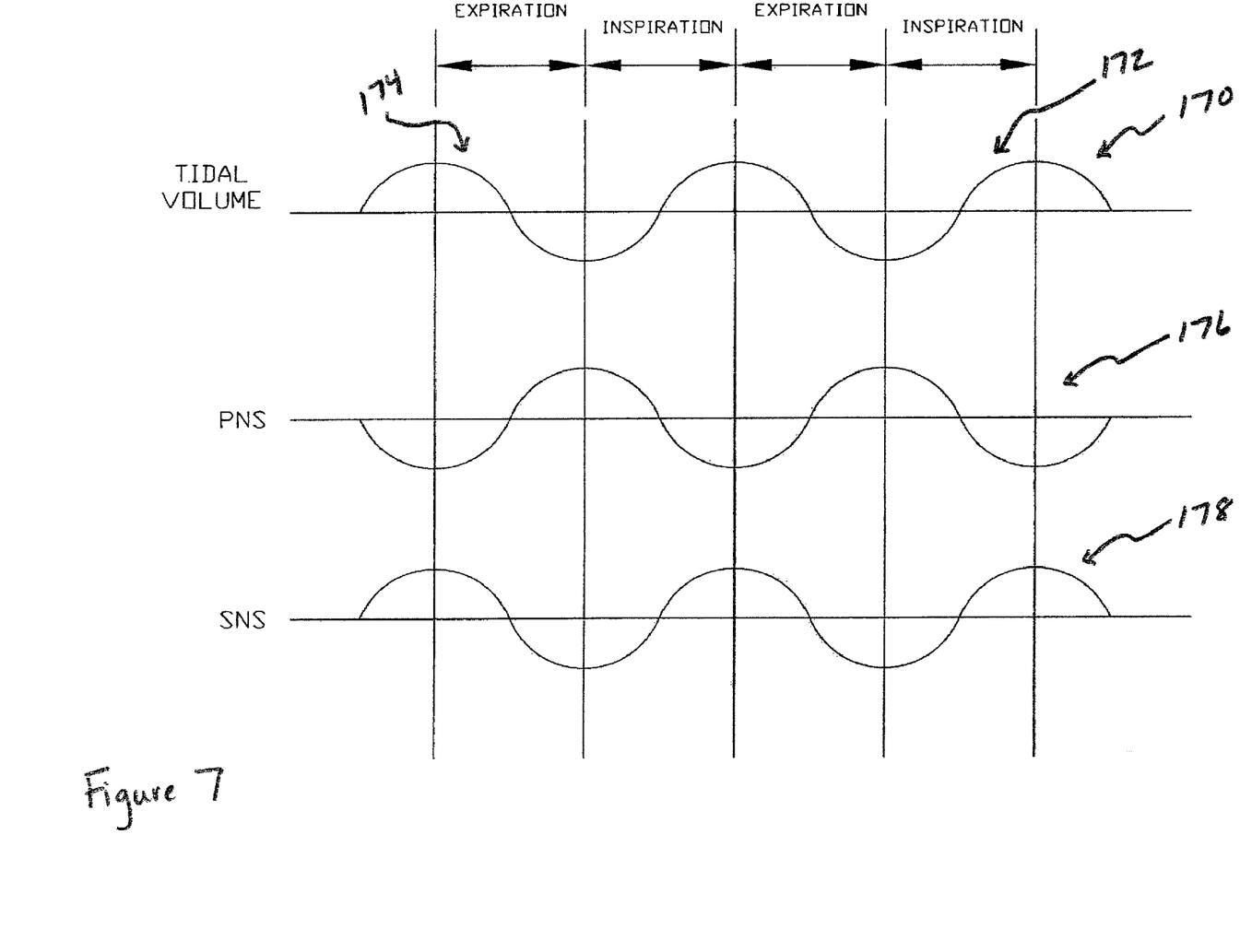
FIG. 7 is a graph illustrating a relationship between respiration, parasympathetic nervous system activity and sympathetic nervous system activity.
Figure 8:
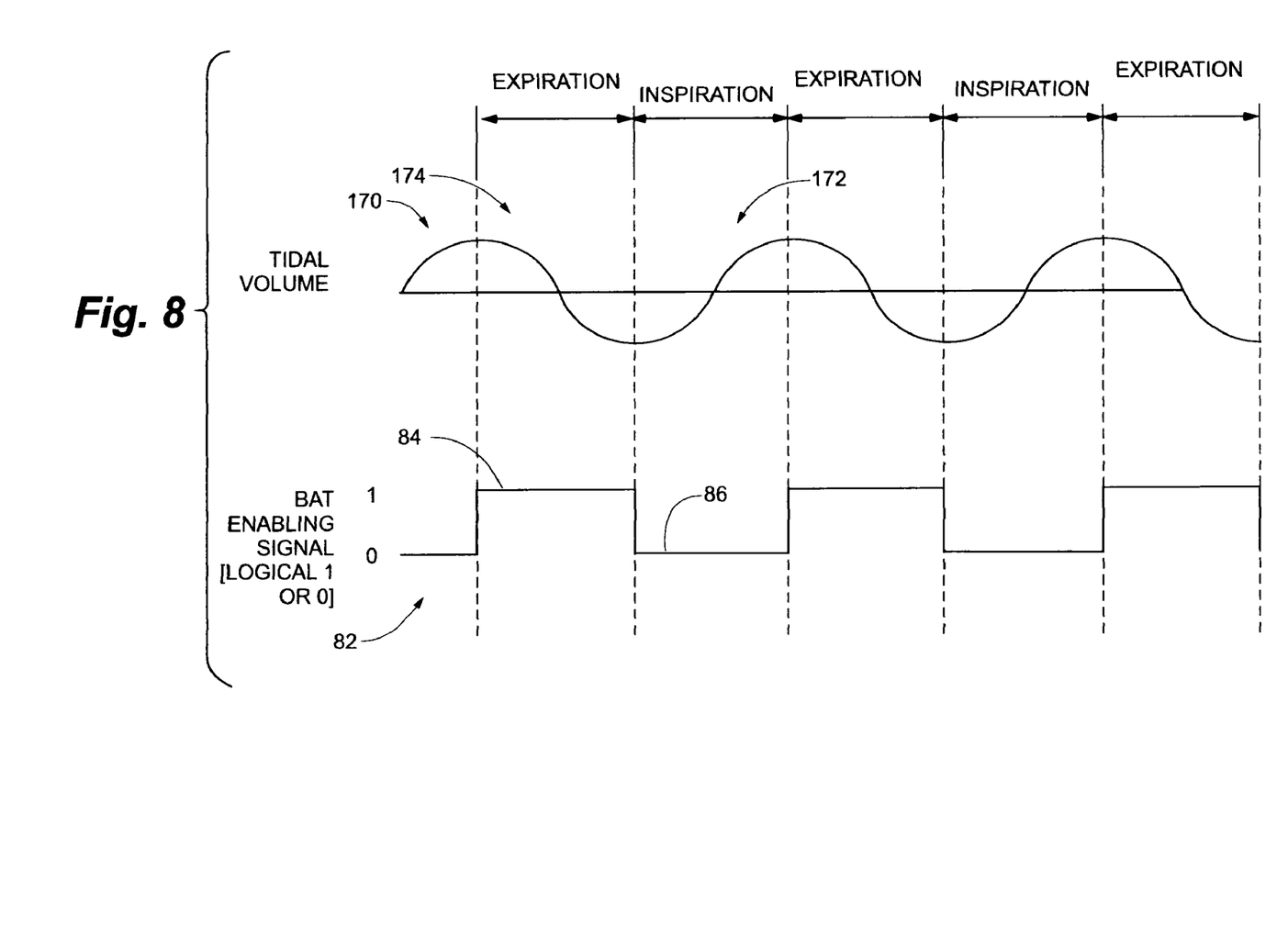
FIG. 8 is a graph illustrating a method of baroreflex modulation therapy according to an embodiment of the present invention.

FIG. 7 depicts a graph illustrating a relationship between respiration, sympathetic nervous system activity and parasympathetic nervous system activity. Respiration is represented by a tidal volume waveform 170 covering a number of respiratory cycles, each including an inspiration phase 172 and an expiration phase 174. As can be seen in the Figures, parasympathetic nervous system activity 176 is generally elevated during the expiratory phase of the respiratory cycle, while sympathetic nervous activity 178 tends to peak during the inspiratory phase. Thus, in one embodiment shown in FIG. 8, baroreflex therapy pulses 184 can be delivered during the expiration phase in order to complement the natural parasympathetic nervous system activity of the body. This can allow the baroreflex modulation therapy device to achieve the same level of therapeutic effect while using less energy.

Figure 9:
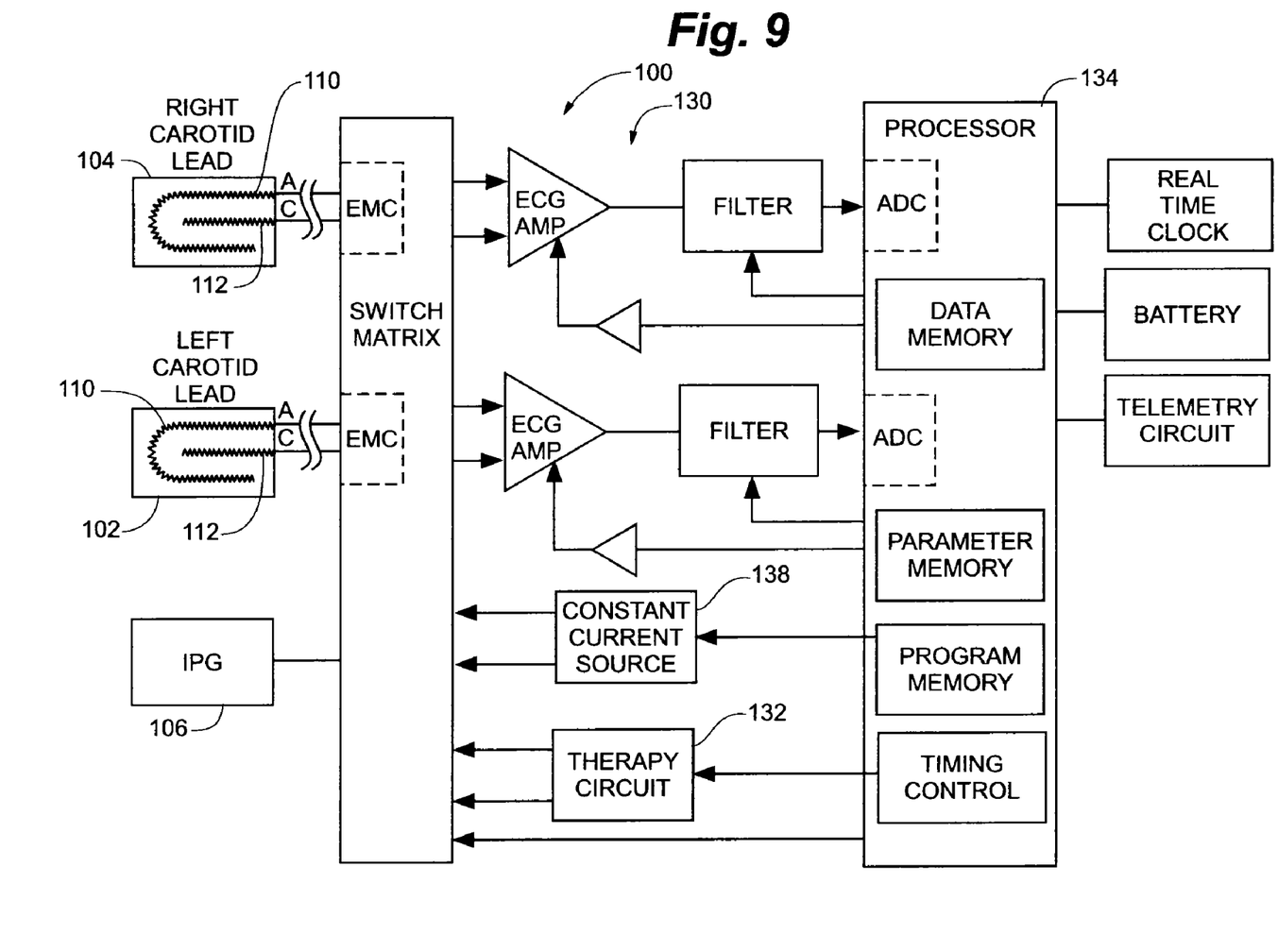
FIG. 9 is a schematic diagram of a baroreflex modulation therapy system according to an embodiment of the present invention.

In one embodiment, a baroreflex therapy system 100 configured to delivery therapy in accordance with the respiration cycle of a patient can have respiration monitoring circuitry 136 as shown in FIG. 9. Respiratory monitoring circuitry 136 can be used with leads 102, 104 and IPG 106 to monitor, for example, impedance changes in the body of the patient that are indicative of respiratory activity. Impedance patterns change during respiration as air enters and leaves the thoracic cavity (lungs) during inspiration and expiration. In one embodiment, leads 102, 104 are implanted into the left carotid sinus and right carotid sinus, respectively. Respiratory monitoring circuitry 136 may work in cooperation with a constant current source 138 to monitor impedance across at least three vectors using leads 102, 104 and IPG 106. Alternatively, system can have only ECG measuring circuitry 130 and no distinct respiration monitoring circuitry 136. In such an embodiment, a patient's respiration cycle can be determined from the ECG measurements, as is known in the art.

Figure 10:
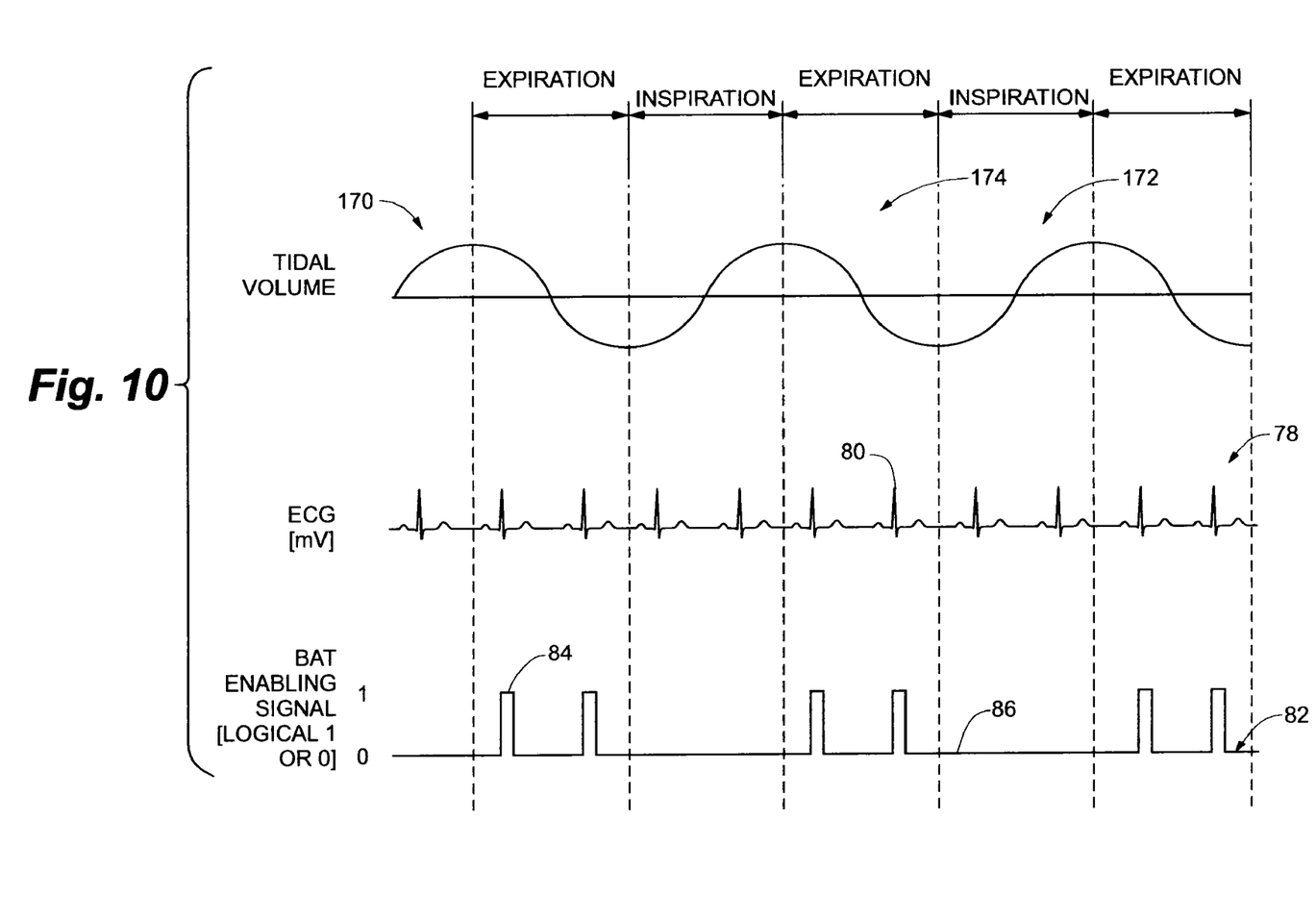
FIG. 10 is a graph illustrating a method of baroreflex modulation therapy according to an embodiment of the present invention.

Referring now to FIG. 10, baroreflex modulation therapy can be provided to take advantage of both the relationship between respiration and autonomic nervous system activity and the relationship between cardiac activity and autonomic nervous system activity. In the embodiment depicted in FIG. 10, therapeutic pulses 84 are delivered during the expiration phase 174 of respiration and shortly after the R-wave 80 during the systolic phase of each cardiac cycle. This provides therapeutic pulses in concert with both the cardiac and respiratory cycles, as described above. This can provide an even further reduction in the energy needed to provide effective therapy.

In another embodiment, the effectiveness of a given therapy may be evaluated by monitoring one or more physiologic parameters of a patient based on an impedance measurement taken across at least three vectors. The delivered therapy may comprise a cardiac rhythm management (CRM) therapy. In such an embodiment, an implantable pulse generator is provided, having at least two leads. A first lead is implanted and configured to deliver a CRM therapy. A second lead is coupled to a monitoring device according to one aspect of the present invention, the monitoring device having one or more electrodes and configured to measure impedance. The monitoring device may be disposed intravascularly, extravascularly, or transvascularly, depending on the desired application. The measured vascular impedance is used to provide one or more patient parameters, upon which the CRM therapy may be adjusted or modified. Other delivered therapies may include neural stimulation and/or modulation therapies, renal therapies, drug delivery therapies, left ventricular assist devices, heart wraps, other mechanical therapies, thermal therapies, or any other therapy having a measurement component in addition to a therapy component.

Figure 11:
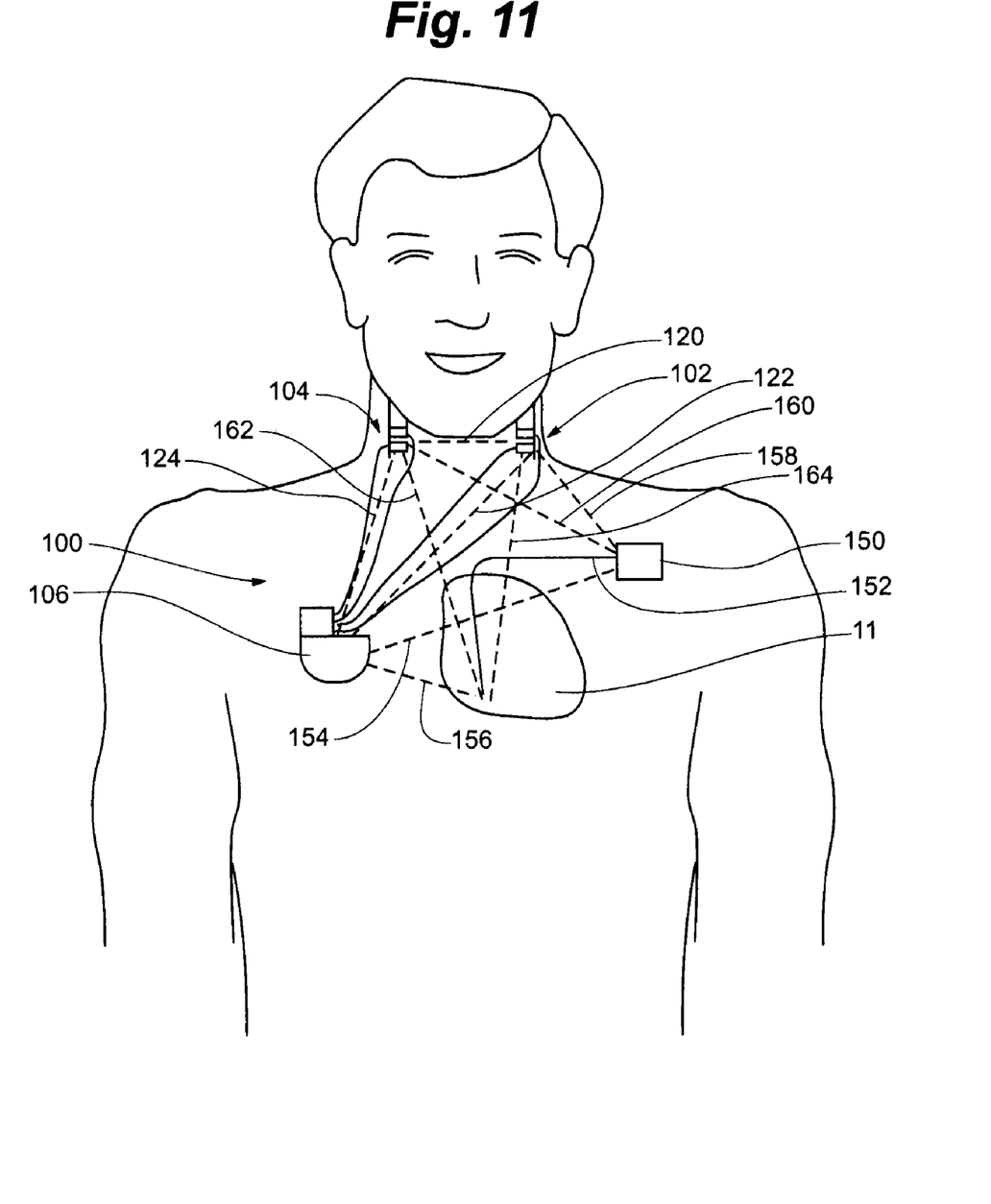
FIG. 11 is a simplified schematic view of a baroreflex therapy device according to an embodiment of the present invention implanted in a patient.

In another embodiment depicted in FIG. 11, additional measurement vectors can be utilized for patient that has another implantable device, such as a pacemaker 150 having a lead 152 inserted into the heart 11, in addition to a baroreflex device having an IPG 106 and first 102 and second 104 leads. Thus in addition to measurement vectors 120, 122 and 124 between the IPG 106 and its two leads 102, 104, there can be at least six additional measurement vectors, including two vectors 154, 156 between the IPG 106 and the pacemaker 150 and the IPG 106 and the lead 152 and four vectors 158, 160, 162, and 164 between each lead 102, 104 and the pacemaker 150 and each lead 102, 104 and the pacemaker lead 152. This can allow for even more precise readings of patient physical parameters.

In a related embodiment, IPG 106 may be configured to provide not only baroreflex therapy, but also CRM therapy such as pacing. IPG 106 therefore includes not only first lead 102 and second lead 104, but also one or more cardiac leads 152. In such an embodiment, additional measurement vectors exist between IPG 106 and cardiac lead 152, lead 102 and cardiac lead 152, and lead 104 and cardiac lead 152.

In one embodiment, instructions for implanting the system in accordance with the various embodiments described herein in the form of printed or electronically, optically or magnetically stored information to be displayed, for example, are provided as part of a kit or assemblage of items prior to surgical implantation of the system. In another embodiment, instructions for implanting the system 10 in accordance with the various embodiments described herein are provided, for example, by a manufacturer or supplier of system, separately from providing the system, such as by way of information that is accessible using the Internet or by way of seminars, lectures, training sessions or the like.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A method for monitoring physiological cycles of a patient, comprising:
    implanting a monitoring system into the patient, the system including a monitoring device operably connected to a first lead and a second lead, each lead having at least one electrode;
    measuring at least one signal indicative of a physiological parameter of the patient along at least three distinct vectors, a first vector defined by an electrode of the first lead and an electrode of the second lead, a second vector defined by the electrode of the first lead and an electrode integrated into an implantable pulse generator, and a third vector defined by the electrode of the second lead and the electrode integrated into the implantable pulse generator; and
    providing an output indicative of the at least one signal indicative of the physiological parameter, wherein implanting the monitoring device is performed such that the first lead is positioned on the left carotid sinus and the second lead is positioned on the right carotid sinus.

2. The method of claim 1, wherein measuring the at least one signal indicative of the physiological parameter measures a voltage.

3. The method of claim 2, wherein providing an output includes providing an electrocardiogram waveform of the voltage.

4. The method of claim 1, wherein measuring the at least one signal indicative of the physiological parameter measures an impedance.

5. The method of claim 4, wherein providing an output includes providing an output representing a respiration cycle of a patient determined from the impedance.

6. A method comprising:
    providing a monitoring system including a monitoring device operably connected to a first lead and a second lead, each lead having at least one electrode; and
    providing instructions, comprising:
        implanting the monitoring system into the patient;
        measuring at least one signal indicative of a physiological parameter of the patient along at least three distinct vectors, a first vector defined by an electrode of the first lead and an electrode of the second lead, a second vector defined by the electrode of the first lead and an electrode integrated into an implantable pulse generator, and a third vector defined by the electrode of the second lead and the electrode integrated into the implantable pulse generator; and
        receiving an output indicative of the at least one signal indicative of the physiological parameter,
    wherein the instructions include positioning the first lead on the left carotid sinus and the second lead on the right carotid sinus.

7. The method of claim 6, wherein measuring the at least one signal indicative of the physiological parameter measures a voltage.

8. The method of claim 7, wherein providing an output includes providing an electrocardiogram waveform of the voltage.

9. The method of claim 6, wherein measuring the at least one signal indicative of the physiological parameter measures an impedance.

10. The method of claim 9, wherein providing an output includes providing an output representing a respiration cycle of a patient determined from the impedance.

* * * * *